United States Patent [19]
Coble et al.

[11] Patent Number: 5,089,961
[45] Date of Patent: Feb. 18, 1992

[54] APPARATUS AND METHOD FOR VASCULAR EXAMINATION OF A LIMB

[75] Inventors: Stephen J. Coble; Edward J. Arkans, both of Sunland, Calif.

[73] Assignee: ACI Medical Incorporated, Sun Valley, Calif.

[21] Appl. No.: 385,329

[22] Filed: Jul. 24, 1989

[51] Int. Cl.⁵ .............................................. G06F 15/00
[52] U.S. Cl. .............................. 364/413.02; 128/691; 128/694
[58] Field of Search ...................... 364/413.02, 413.03; 128/694, 691

[56] References Cited

PUBLICATIONS

Christopoulos, D. G. et al., "Air-Plethysmography and the Effect of Elastic Compresion on Venous Hemodynamics of the Leg", *Journal of Vascular Surgery*, vol. 5, No. 1, pp. 148-159 (Jan. 1987).
Product information literature entitled "Phleborheograph: The New PRG for Venous and Arterial Procedures", by Cranley-Grass, Grass Instrument Co., 4 pages (1982).
Cranley, John J. et al., "The Cranley-Grass Phleborheograph", The Grass Instrument Co., Quincy, Mass., 43 pages (1984).

*Primary Examiner*—Dale M. Shaw
*Assistant Examiner*—Laura Brutman
*Attorney, Agent, or Firm*—Nilsson, Robbins, Dalgarn, Berliner, Carson & Wurst

[57] ABSTRACT

An apparatus and a method are provided for vascular examination of a limb by inflation of a flexible-walled pneumatic chamber mounted to the limb and calibration of the pressure within the chamber in units of volume. Calibration is accomplished by inflating the chamber to a preselected reference pressure, altering the volume of the chamber, and measuring the calibration pressure at the altered volume. The calibration pressure is stored for use off-line in scaling subsequent pressure fluctuations as changes in limb volume.

24 Claims, 5 Drawing Sheets

APPARATUS AND METHOD FOR VASCULAR EXAMINATION OF A LIMB

BACKGROUND OF THE INVENTION

The present invention relates to an air-plethysmograph for vascular examination of limbs. More particularly, it pertains to a calibrated apparatus and method for measuring limb volume changes through changes in pressure in a closed pneumatic system.

Reconstructive surgery of deep veins, and a continuing controversy about the mechanism of the effect of elastic compression on venous hemodynamics in the lower limb, have created a need for a noninvasive measurement of reflux and calf muscle pump ejection. Plethysmographs have been used to study limb muscle pump function by determining pressure changes in a cuff surrounding a limb due to postural changes and exercise.

A prior form of plethysmograph, disclosed by Christopoulos et al. in "Air-plethysmography and the effect of elastic compression on venous hemodynamics of the leg", *Journal of Vascular Surgery*, Vol. 5, No. 1, pg. 148-159, January 1987, consists of an air chamber which surrounds a limb and is inflated to a pressure sufficient to ensure good contact with the limb. Because pressure and volume are inversely related in a closed system, and be the volume of the air chamber is inversel related to the volume of the limb that it surrounds, pressure in the air chamber is directly proportional to the volume of blood in the limb. Problems arise in calibrating the pressure to volume units, however, as attempted by Christopoulos et al., with a second chamber between the air chamber and the limb. The air chamber is initially inflated and closed off from the atmosphere while the limb is kept in an elevated position. After a preselected waiting period, the pressure in the air chamber is measured. A calibration is then performed by injections of known volumes of water into the second chamber. The pressure in the air chamber is measured after each injection, yielding a water volume calibration curve which correlates air chamber pressure with increases in water volume. The water is then removed from the second chamber and vascular examination is conducted. During examination the patient is asked to perform various tests, such as arterial inflow and venous obstruction tests, and the pressure within the air chamber is recorded by a chart recorder. Attempts are made to match recorded pressures with volumes using the volume calibration curve.

Unfortunately, the use of water in the second chamber of Christopoulos et al. complicates the procedure and disrupts the temperature gradient between the air chamber and the limb. This can cause significant output errors. The arbitrary units of the pressure signal also make it difficult to read in terms of volume. Volumes are known at specific points, but interpolation is difficult.

Other devices of this type have a small syringe (~1 cc) in communication with an air chamber for injecting a known amount of air into a cuff. The injection of air acts as a reduction in system volume which calibrates the chart for a 1 cc increase in limb volume. However, these devices are calibrated "on line", like the Christopoulos et al. device, and do not produce a one-to-one correspondence between divisions on the chart and units of displayed volume.

Therefore, it is desirable in many applications to provide an apparatus and a method for easily calibrating the output of a plethysmograph to limb volume over a range of volumes and reducing output errors.

SUMMARY OF THE INVENTION

The present invention simplifies calibration of an air-plethysmograph to reflect limb volume and permits calibration over a range of operation so that each increment of distance on the chart corresponds to a known volume change. Calibration takes place "off-line" using pressure measurements taken at a first reference volume and a second calibration volume resulting from a controlled alteration of system volume. Ongoing volume fluctuations due to changing conditions in the cuff and the patient's limb do not affect calibration. This eliminates significant errors during calibration and allows the gain and offset of the output signal to be adjusted accurately.

Another distinct advantage of the present invention over prior plethysmographs is that the reference pressure level is maintained dynamically for a period long enough for temperature, arterial inflow and relaxation of the cuff to stabilize. Air is added and released in the air chamber during this period, as necessary, to achieve an accurate base line from which calibration and subsequent volume measurements can be made.

Specifically, the present invention comprises an apparatus and a method for vascular examination of a limb in which: at least one flexible-walled chamber of a pneumatic system is mounted to a limb for monitoring limb volume; the pneumatic system, and thus the flexible-walled chamber, are inflated to a preselected reference pressure at a stable reference volume; the pneumatic system is closed to the atmosphere; the volume of the pneumatic system is altered by a preselected amount to achieve a calibration volume and a corresponding calibration pressure; the calibration pressure is measured and stored; and, fluctuations in system pressure relative to the reference pressure are displayed as changes in limb volume.

In a preferred embodiment, the reference pressure is stored for use with the calibration pressure in calibrating subsequent fluctuations. In another embodiment, the fluctuations are displayed on a graphical output device calibrated to reflect changes in limb volume by: sending signals representative of the reference pressure and the calibration pressure to the output device for display; and, adjusting the gain of those signals so that the reference pressure and the calibration pressure are displayed a preselected distance apart in a direction representing limb volume. The signals can then also be adjusted so that the reference pressure is displayed at a preselected baseline level corresponding to the reference volume. This is accomplished by sending the reference pressure and the calibration pressure signals alternately to the output device for display during calibration in the absence of any other pressure signal. Thus, calibration takes place while the output device is "off line".

Yet another embodiment of the invention involves sensing the pressure in the pneumatic system and maintaining it at the reference pressure for a preselected stabilization period to permit conditions within the flexible-walled chamber and the limb to stabilize. The pneumatic system is maintained during the stabilization period by introducing and withdrawing air, as necessary, to achieve stable temperature and volume conditions.

BRIEF DESCRIPTION OF THE DRAWINGS

The above and other features of the present invention may be more fully understood from the following detailed description, taken together with the accompanying drawings, wherein similar characters refer to similar elements throughout and in which.

DESCRIPTION OF THE PREFERRED EMBODIMENTS

Figure 1:
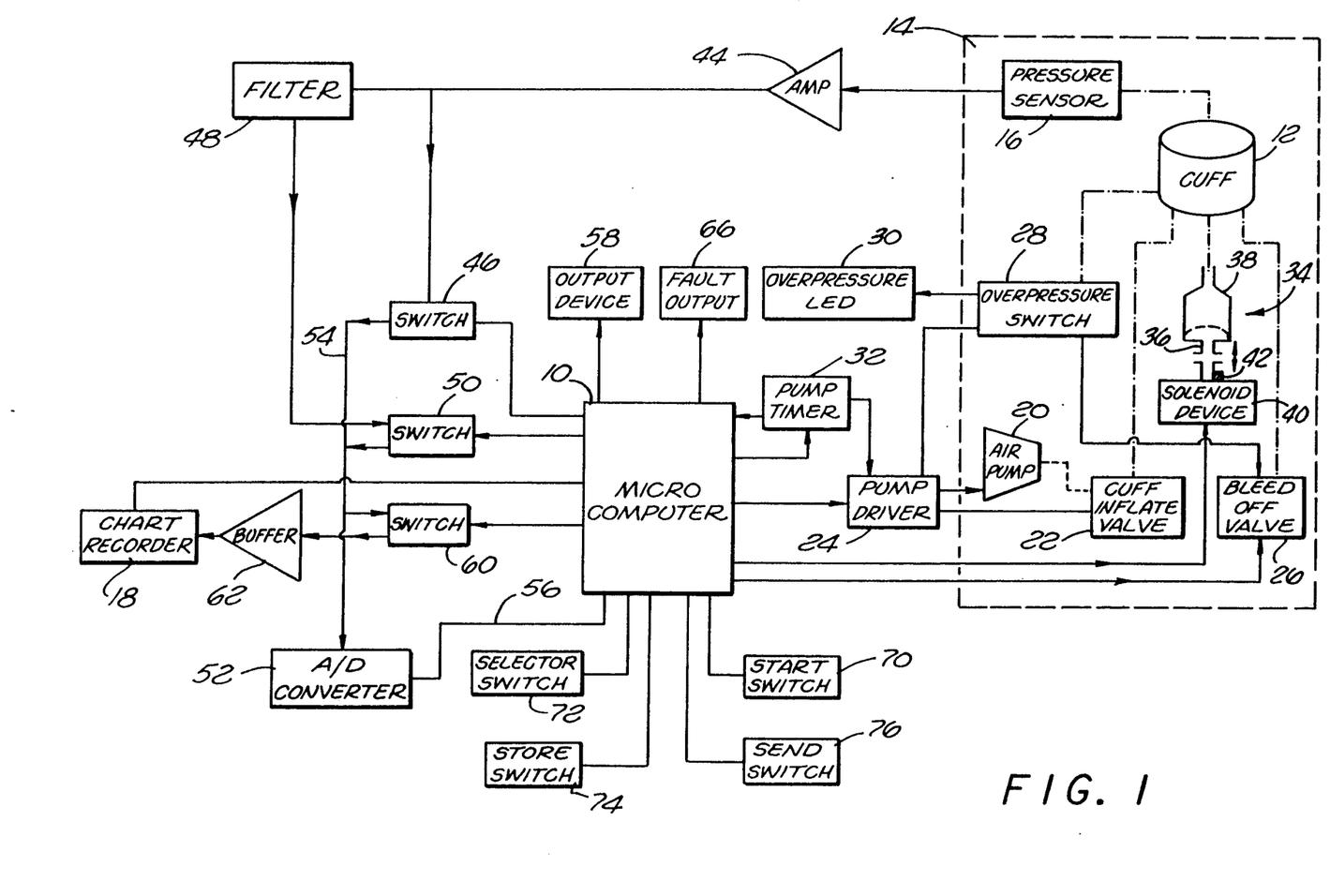
FIG. 1 is a schematic diagram of an apparatus constructed according to a preferred embodiment of the present invention for vascular examination of a patient's limb.

Referring to FIG. 1, a preferred form of apparatus constructed according to the present invention for vascular examination of a patient's limb has a microcomputer 10 which monitors the pressure of air in a flexible-walled chamber or cuff 12 of a pneumatic system 14 through a pressure sensor 16. The microcomputer 10 displays the pressure of the pneumatic system 14 on a chart recorder or other suitable output device 18 as a signal calibrated to the volume of a limb surrounded by the cuff 12.

Calibration is accomplished by reducing the volume of the system from a reference volume at which the pressure of the pneumatic system 14 is a known, stabilized value to an altered volume which differs from the reference volume by a known amount, preferably 100 ml. Storage of system pressure at both the reference volume and the altered volume, and knowledge of the difference between the volumes, permit the chart recorder 18 to be calibrated by adjusting the pressure signal so that subsequent fluctuations in pressure are displayed on a graph having a known number of divisions for each unit of limb volume. Calibration is performed by outputting the reference and calibration pressure levels alternately to the chart recorder 18 and making appropriate adjustments to either the pressure signal or the gain and offset of the recorder.

The cuff 12 is part of the pneumatic system 14 and may be any suitable flexible-walled chamber designed for placement around a limb. Typically, it is an air cuff such as a 14-inch long toroidally-shaped polyurethane bag capable of surrounding a lower leg from the ankle to just below the knee so that a change in leg volume due to vascular activity causes an equal and opposite change in volume of the cuff. For this purpose, the outer wall of the cuff should be relatively insensitive to changes in cuff pressure within the range encountered in use.

Pressure in the cuff 12 is maintained by an air pump 20 acting through a cuff inflate valve 22. The air pump 20 and the cuff inflate valve 22 are both part of the pneumatic system 14. The microcomputer 10 controls the inflation process with a pump driver 24. Inflation begins with the microcomputer 10 signalling the pump driver 24 to start the air pump 20 and open the cuff inflate valve 22. When a desired pressure is achieved, the microcomputer 10 closes the pneumatic system 14 by signalling the pump driver 24 to stop the air pump 20 and close the cuff inflate valve 22. Pressure in the cuff 12 can be released through a bleed-off solenoid valve 26 which communicates with the cuff 12 and is controlled by the microcomputer 10. As described more fully below, the air pump 20 and the bleed-off valve 26 may be actuated alternately, as needed, in a pressure stabilization mode of the apparatus to achieve a stable reference volume at a preset reference pressure.

Pressure in the cuff 12 is constantly monitored by an "overpressure" switch 28 of the pneumatic system 14. When the pressure in the cuff 12 exceeds a maximum preset limit, the overpressure switch 28 signals the pump driver 24 to deactivate the air pump 20. The overpressure switch 28 also opens the bleed-off valve 26 to release air from the cuff 12 and triggers an overpressure LED 30 to signal that the pressure has exceeded its limit.

The microcomputer 10 is also monitored during inflation by a watch dog or pump timer 32. The microcomputer 10 starts the pump timer 32 each time it activates the pump driver 24. The pump timer 32 times out at a preselected time-out interval. If the microcomputer 10 fails to stop and restart the pump driver 24 at intervals less than the time-out interval of the pump timer 32, the pump timer 32 turns off the pump driver 24, and resets the microcomputer 10. This ensures that the air pump 20 will not stay on in the event of a microcomputer 10 failure.

Each time the microcomputer 10 activates the pump driver 32, the microcomputer 10 checks the pressure level to determine if there is an appropriate rise in the pneumatic system pressure. If the microcomputer 10 detects no rise in pressure, or a decrease in pressure shortly after activating the pump driver 24, the microcomputer 10 goes into a "fault" condition, indicating either a pneumatic system leak or a faulty air pump 20 or pump driver 24.

The pneumatic system 14 also includes a calibration syringe or other mechanism 34 having a piston or plunger 36 which moves axially within a cylinder 38 to enlarge or reduce the volume of the system. In a preferred embodiment, the plunger 36 of the calibration syringe 34 is actuable by a solenoid or motor device 40 in response to signals from the microcomputer 10. Thus, the microcomputer 10 can be used to control the volume of the pneumatic system 14 between an initial reference volume corresponding to a retracted condition of the plunger 36 and a smaller calibration volume corresponding to a bottomed-out condition of the plunger 36. The plunger 36 is preferably provided with a mechanical stop 42 in order to accurately fix the reference volume. In another embodiment, the calibration syringe 34 may be a simple syringe which is controlled manually by an operator.

The pressure transducer or sensor 16 may be connected to the cuff 12 by a length of tubing, or may be placed on or near the cuff 12. In either case, it is exposed at a sensing surface thereof to the pressure within the pneumatic system 14. The pressure sensor 16 therefore generates an analog pressure signal proportional to the system pressure.

The pressure signal is conditioned by an amplifier 44, after which it is applied directly to an analog switch 46 and through a low pass filter 48 to an analog switch 50. The analog switches 46 and 50 are both controlled by the microcomputer 10 to selectively apply the pressure signal to an analog-to-digital (A/D) converter 52 along a common output line 54. The only difference between these paths is that the signal applied through the analog switch 50 is filtered while that applied through the analog switch 46 is not. The filter 48 decreases sensed pressure variations known as "pump artifacts" which are inherent in reciprocating air pumps and enables a stable pressure to be sensed while the system is pumping. Thus, the microcomputer 10 can selectively apply a filtered or unfiltered pressure signal to the A/D converter 52.

The digitized pressure signal from the A/D converter 52 is applied to the microcomputer 10 along a line 56 for use in controlling the apparatus and for calculating the magnitude of changes in limb volume. Such calculated volumes are applied to an output device 58, which may be any form of conventional readout mechanism, including a digital display, a graphical display or a mechanical or electrical bar graph.

In addition to being applied to the microcomputer 10, the analog pressure signal along the line 54 can be applied to the chart recorder 18 through a third analog switch 60 and a buffer 62. This provides a direct graphical readout of system pressure, and therefore volume, whenever the analog switch 60 is energized. This output can be calibrated and scaled automatically, if desired, by the microcomputer 10 which controls the gain and offset of the chart recorder 18 along a control line 64.

The microcomputer 10 also has a fault output 66. The microcomputer 10 activates the fault output 66 when an error, such as a ROM or RAM error, occurs in the microcomputer 10.

Figure 2A:
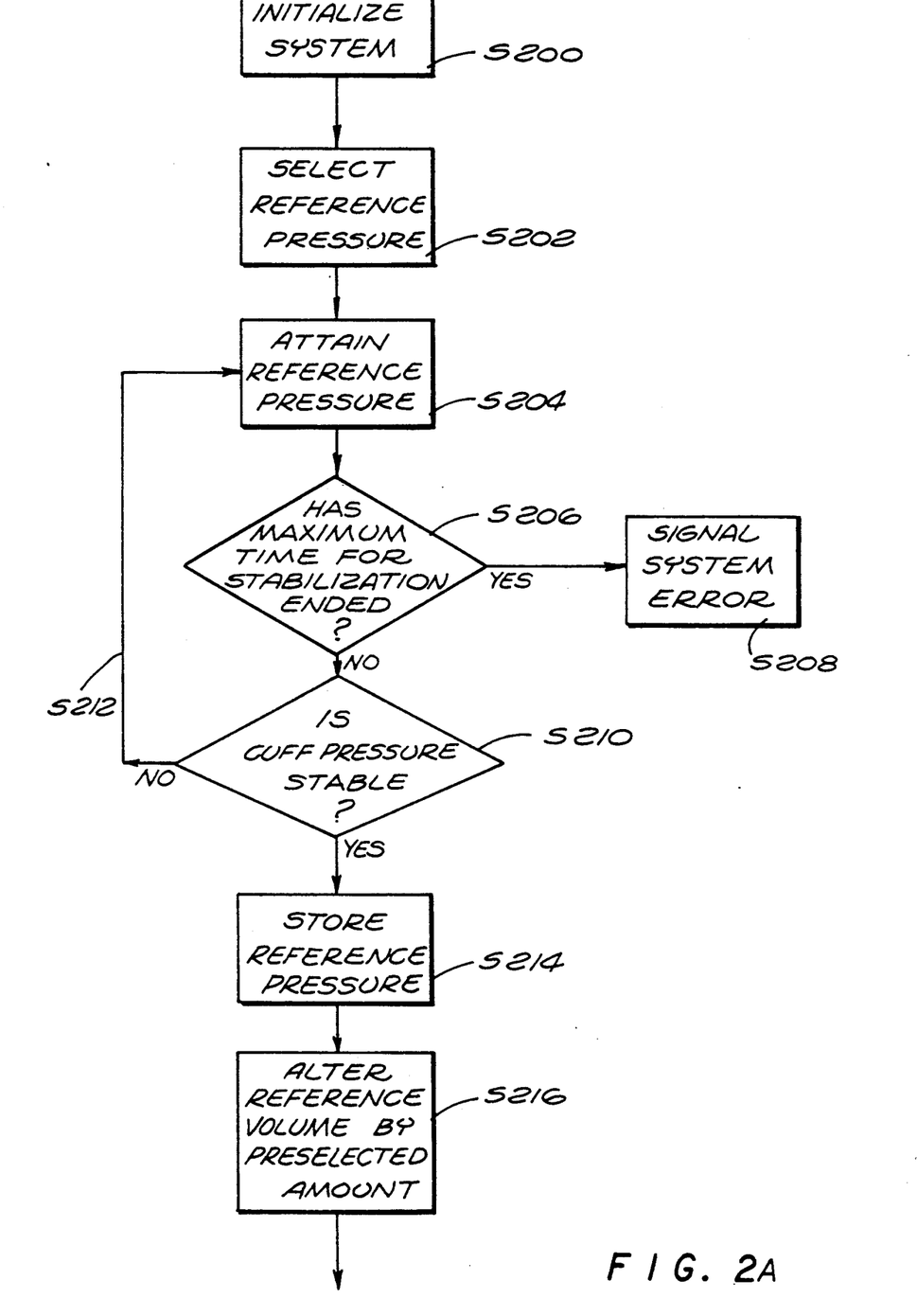
FIGS. 2A and 2B are two portions of a flow chart illustrating a preferred method of vascular examination using the apparatus of FIG. 1.
Figure 2B:
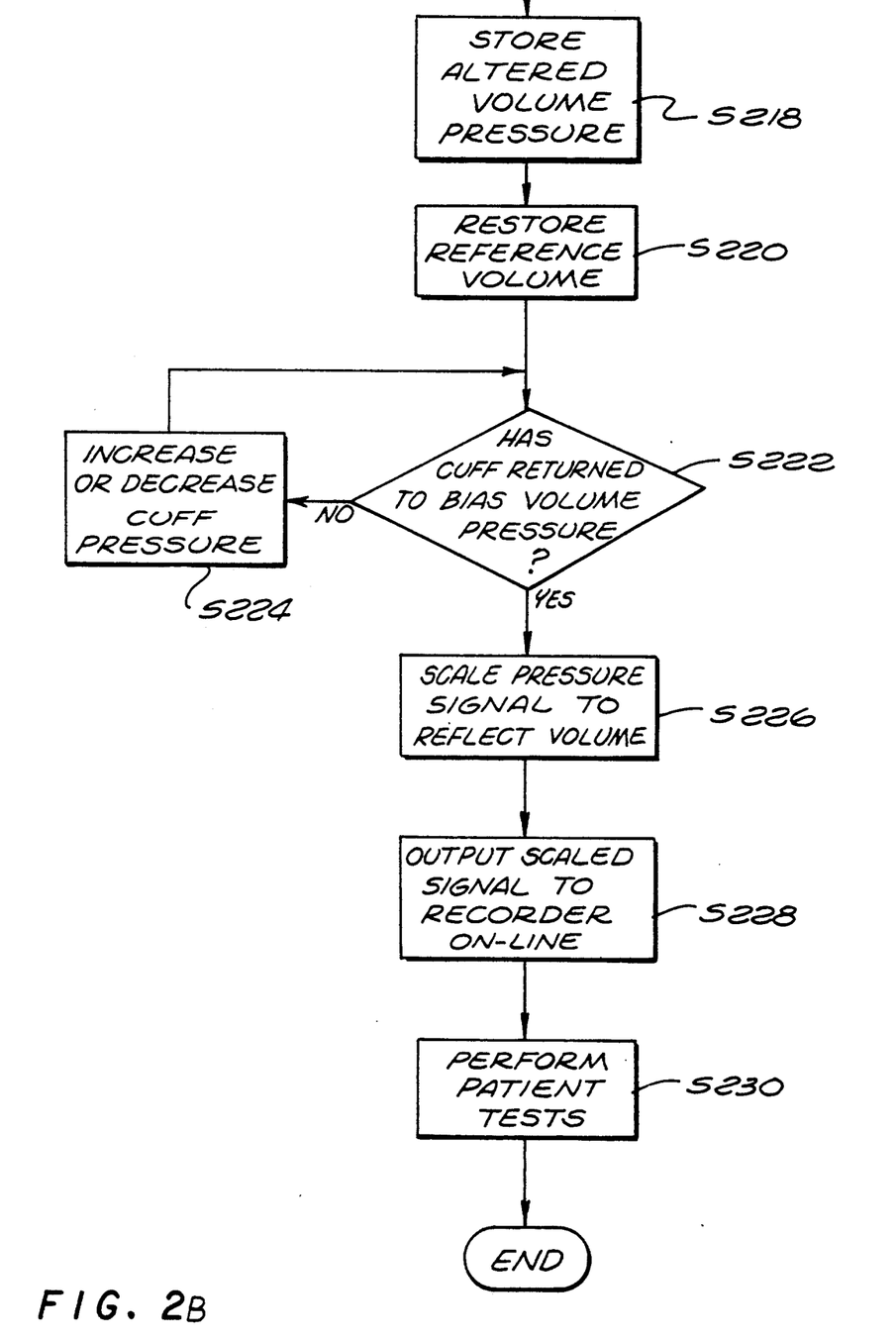

FIGS. 2A and 2B are flow charts of a method performed by the air-plethysmograph apparatus of FIG. 1. The procedure begins with initialization at step 200, which is begun by depressing a start switch 70 (see FIG. 1). This powers up the microcomputer 10 and causes it to perform an internal self-test routine. Failure of any of the self-tests causes the microcomputer 10 to deactivate the system and trigger the fault output 66. Thus, the pump driver 24 is de-energized and the bleed-off valve 26 is opened to deflate the cuff 12.

If the self-tests are all passed, a reference pressure is selected in step 202 by moving a thumb wheel or other mechanism of a reference pressure selector switch 72. The reference pressure is chosen to be high enough to ensure good contact between the cuff and the limb but not so high that it significantly alters the hemodynamics within the limb. A pressure of 6 mm Hg is typically used.

Once the reference pressure is selected, the cuff 12 is inflated and maintained at the reference pressure to permit the temperature gradient between the limb, the cuff 12 and the surrounding air to stabilize and ensure a resting arterial inflow to the limb. The limb is typically elevated to empty the veins and the patient is asked to keep as still as possible.

In the first step of the inflation phase, step 204, the microcomputer 10 transmits an activation signal to the pump timer 32 and the pump driver 24. In turn, the pump driver 24 opens the cuff inflate valve 22, signals the air pump 20 to begin pumping air into the cuff 12, and activates the pump timer 32. If the time to attain a stable reference pressure ever exceeds a preselected maximum time for stabilization of the cuff pressure (step 206), indicating a malfunction in the pneumatic system 14, the pump timer 32 signals the microcomputer 10 that an error has occurred (step 208). The microcomputer 10 then deactivates the pump driver 24 and opens the bleed-off valve 26 to release the cuff pressure.

In step 210 the microcomputer 10 monitors the digital representation of the pressure signal received from the A/D converter 52 to identify when the pressure signal becomes stable over a preselected period of time sufficient to reach the temperature and arterial flow conditions described above. The preselected period is preferably approximately 5 minutes. Any deviation from the reference pressure signal during this period causes the processor to return to step 204 along a path 212 to correct for the deviations. The pneumatic system 14 is thus returned to the reference pressure by activating the pump driver 24 to add air or activating the bleed-off valve 26 to release air from the system, as required.

While the exact sequence of steps by which system pressure is maintained at the reference level may vary from one embodiment to the other, it has been found desirable to operate the air pump 20 and the cuff inflate valve 22 in a two-phase manner. When the sensed pressure falls short of the reference pressure by more than a preselected amount, the filtered signal is sensed while the air pump 20 is on. After the pressure increases to a level within the preselected amount of the reference pressure, the system enters a second phase in which the air pump 20 stops momentarily and the system senses the unfiltered signal while the air pump 20 is stopped to obtain more accurate pressure readings.

When the cuff pressure remains at the reference level for the preselected period of time without requiring the addition or withdrawal of air, the system is stabilized. The microcomputer 10 then passes to step 214 and stores the reference pressure in memory.

After the reference pressure is stored, the volume of the pneumatic system 14 is altered by a preselected amount (step 216) and the pressure at the altered volume is stored in memory (step 218). This provides a second point at which system pressure is known in relation to system volume which itself is inversely related to changes in volume of the limb within the cuff 12. The two calibration pressure points therefore define a linear relationship between system pressure (P) and limb volume (V) which allows subsequent pressure changes to be expressed as changes in limb volume.

Although the volume of the pneumatic system can be either increased or decreased in step 216, it is typically decreased by approximately 100 ml. This provides a second data point which, in calibration with the reference pressure, defines a range of pressures within which the system can operate to measure increases in volume of a patient's limb. The decrease in volume is accomplished in the present embodiment by fully depressing the plunger 36 of the calibration syringe 34.

After the pneumatic system 14 is restored to its reference volume by withdrawal of the plunger 36 (step 220) the system should return to its original reference pressure. However, the actual pressure may differ from the reference pressure due to changes in temperature, deformation of the cuff material, and moderation of arterial inflow during calibration. The microcomputer 10 therefore examines the pressure in step 222 and, if necessary, acts in step 224 to return the system to its original reference pressure by adding or releasing air. Step 224 is identical to step 204 described above.

After the reference volume is restored, the stored values of reference and altered volume pressure are used to scale the output of the apparatus so that it reflects changes in volume of the pneumatic system 14 (step 226). This can be done by altering the signal from the pressure sensor 16 within the microcomputer 10 or by adjusting the gain and offset of the recording instrument (18 or 58). In either case, the goal is to adjust the output so that the distance between the reference and altered volume signals represent a convenient number of unit divisions on the recording instrument and the reference volume signal occurs at an appropriate baseline position. Exemplary methods of accomplishing these goals are discussed below in connection with FIGS. 3A and 3B. The ordinate of the recording instrument can then be marked to represent increments of volume.

Figure 4A:
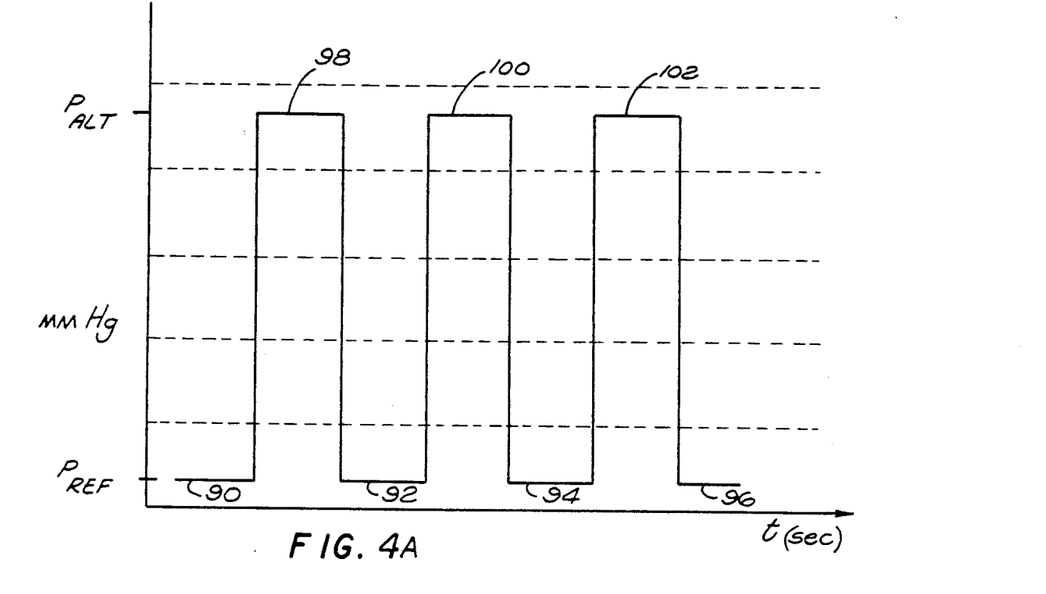
FIG. 4A is a graph of a calibration waveform produced by outputting the reference and calibration pressure levels alternately during a manual calibration procedure of the present invention; and, FIG. 4B is a graph depicting a sample output produced by the hardware of FIG. 1.
Figure 4B:
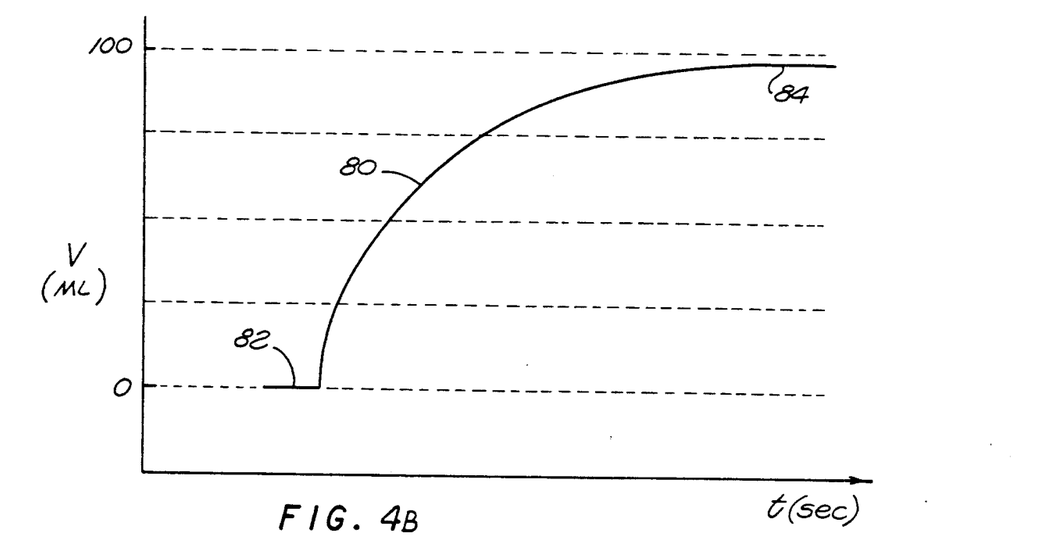

After the pressure signal is scaled, the output of the pressure sensor 16 is sent on-line to the recording instrument for display in calibrated volume units (step 228) while patient tests are performed (step 230). The resulting output, an example of which is shown in FIG. 4B, is an accurate measure of changes in blood volume in the limb of the patient. Referring specifically to FIG. 4B, which is an example of an output resulting from filling of the vascular volume of a leg, an output curve 80 rises from a reference volume level 82 (denoted "zero ml") to a level 84 which is close to the calibrated "100 ml" level.

Except for the initialization step 200 and the pressure selection step 202, all of the steps described above are preferably performed automatically by the microcomputer 10 in the sequence described. The plunger 36 of the calibration syringe 34 is then operated automatically by the microcomputer 10 through the solenoid device 40. In some instances, however, it may be desirable to perform one or more of the steps manually. Thus, steps 214 and 218 can be performed by sequentially depressing a store switch 74 (See FIG. 1) and steps 216 and 220 can be accomplished by depressing and withdrawing, respectively, the plunger 36. The scaling step 226 can also be performed either automatically or manually by depressing a send switch 76 to begin scaling and depressing it again to stop.

Figure 3A:
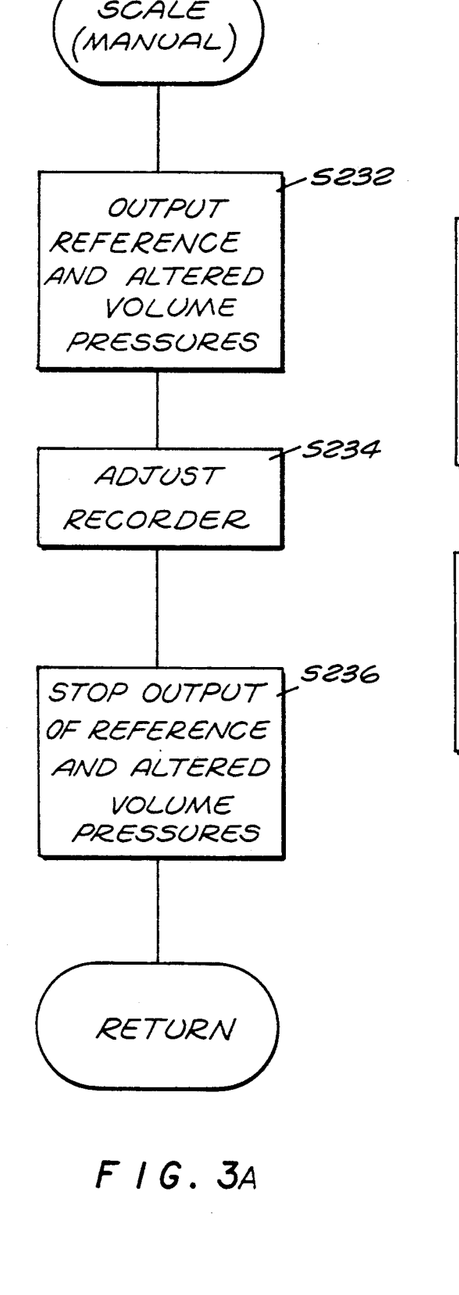
FIGS. 3A and 3B are flow charts illustrating manual and automatic scaling routines, respectively, practiced in a preferred form of the present invention.
Figure 3B:
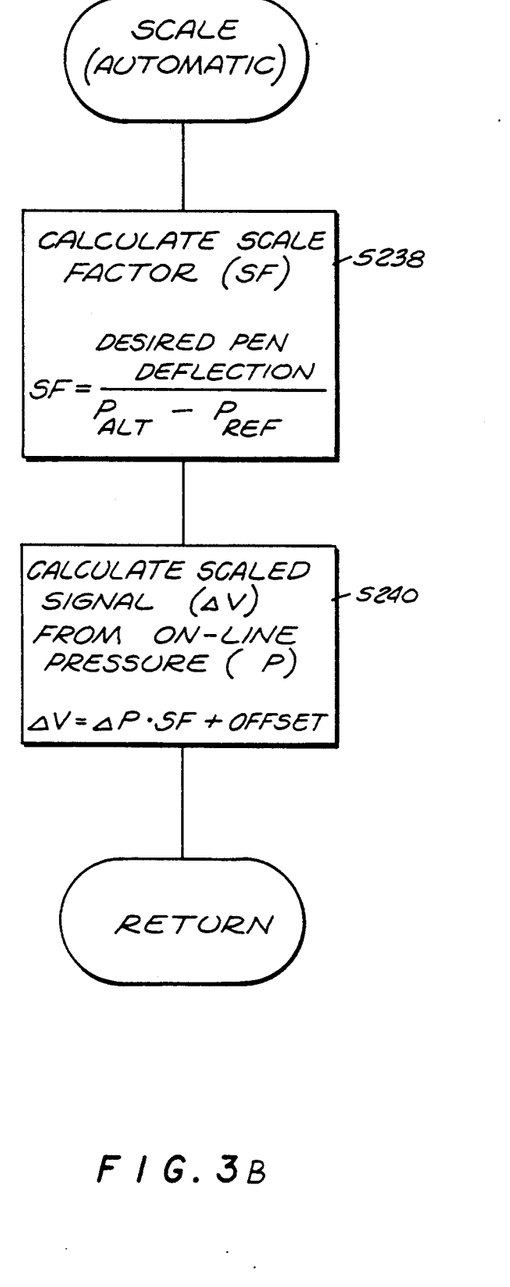

FIGS. 3A and 3B illustrate alternative "subroutines" for scaling the pressure signal as described in step 226. The principal difference is that the subroutine of FIG. 3A is performed manually while that of FIG. 3B is performed automatically. Referring first to FIG. 3A, the manual subroutine begins by alternately outputting the stored reference and altered volume pressure signals to the chart recorder 18 by depressing the send switch 76, both of FIG. 1 (step 232). This gives rise to the calibration waveform of FIG. 4A, wherein 90, 92, 94 and 96 represent the reference pressure signal ($P_{ref}$), and 98, 100 and 102 represent the altered volume pressure signal ($P_{alt}$).

While the calibration waveform is displayed, the operator manually adjusts the "gain" and "offset" of the chart recorder 18 (step 234). The gain is adjusted so that the pen of the chart recorder 18 is displaced vertically a distance corresponding to a convenient number (e.g., four) of divisions of chart recorder paper. The offset is then adjusted to place the reference pressure signal at an appropriate major division of the paper. The calibration waveform is then terminated by depressing the send switch 76 of FIG. 1 (step 236), leaving the apparatus calibrated for on-line operation in steps 228 and 230 of FIG. 2B.

The foregoing description is intended specifically for the case in which the signal is displayed on a chart recorder having a moving pen mechanism. The routine of FIG. 3A is suitable, however, for use with any form of graphical display device which provides a hard copy. For example, a chart recorder having an array of independently addressable thermal heads may be used to print the scale and the output data simultaneously. In such a case, it is necessary only to adjust the gain of the recorder so that the pressure signal output is proportioned to the size of the paper.

Referring to FIG. 3B, automatic scaling of the output signal may be accomplished internally by the microcomputer 10. The microcomputer first calculates a scale factor in step 238 according to the expression:

$$SF = \frac{\text{desired pen deflection}}{P_{alt} - P_{ref}}$$

and then calculates scaled volume information ($V$) from on-line pressure information ($P$) provided by the sensor 16 using the relationship: $V = P \times SF + OFFSET$ (step 240). The scale factor is a constant for any set of measurements because $P_{alt}$ and $P_{ref}$ are stored in the microcomputer 10 and the desired pen deflection for calibration pressure values is known from the characteristics of the chart recorder or other recording instrument 18. The desired location of the baseline pressure signal is selectable in advance and the output required to achieve it is also known from the characteristics of the recording instrument. Thus, the "offset" signal can be calculated automatically, as well.

From the above, it can be seen that a non-invasive pneumatic apparatus and corresponding method have been provided for generating a calibrated display of limb volume over time for vascular examination.

Although described for purposes of clarity with regard to specific preferred embodiments, the present invention is not limited to those embodiments but rather is applicable broadly to all versions falling within the scope and spirit of the appended claims. For example, the calibration syringe described herein can take the form of a piston and cylinder device but may be a rotary device or other mechanism having an internal volume which can be altered repeatedly and reproducibly by a preselected amount. The calibration pressure values also need not be displayed as the square waveform shown in FIG. 4A, but may be a staircase function which would be repeatable at the discretion of the operator during the scaling method. This is particularly useful when a plurality of altered volumes are used to provide more than two calibration data points.

What is claimed is:

1. Apparatus for vascular examination of a limb, comprising:
   a pneumatic system having:
   at least one flexible-walled chamber mountable to a limb for monitoring limb volume;
   a pressure sensor in communication with the flexible-walled chamber for measuring pressure in the system;
   means for inflating the pneumatic system to a preselected reference pressure at a stable reference volume;

a valve for closing the pneumatic system to the atmosphere at said reference pressure; and, means in communication with the flexible-walled chamber for altering the volume of the pneumatic system by a preselected amount to achieve a calibration volume at a corresponding calibration pressure;

memory means for storing the calibration pressure measured by the sensor; and means for using the stored calibration pressure to display fluctuations in system pressure as changes in limb volume;

the inflating means comprising means responsive to the pressure sensor for maintaining the pneumatic system at the reference pressure for a preselected period by introducing and withdrawing air, as necessary, to permit temperature and volume conditions within the flexible-walled chamber and the limb to stabilize.

2. The apparatus of claim 1 which further comprises:
memory means for storing the reference pressure for use with the calibration pressure in calibrating subsequent pressure fluctuations.

3. The apparatus of claim 2 wherein:
the means for displaying pressure fluctuations comprises a graphical output device.

4. The apparatus of claim 3 which further comprises:
means for sending signals representative of the reference pressure and the calibration pressure to the output device for display; and
means for adjusting the gain of said signals so that the reference pressure and the calibration pressure are displayed a preselected distance apart in a direction representing limb volume.

5. The apparatus of claim 4 which further comprises:
means for adjusting said signals so that the reference pressure is displayed at a preselected baseline level.

6. The apparatus of claim 5 wherein:
the means for adjusting the gain of said signals and the means for adjusting said signals so that the reference pressure is displayed at a preselected baseline level are automatic.

7. The apparatus of claim 4 wherein the means for sending the reference pressure and the calibration pressure to the output device comprise:
means for alternately sending the reference pressure and the calibration pressure to the output device for display during gain adjustment.

8. The apparatus of claim 1 which further comprises:
means for returning the pneumatic system to the reference volume after the calibration pressure has been stored.

9. The apparatus of claim 8 wherein the means for altering volume comprise:
a syringe in communication with the pneumatic system.

10. The apparatus of claim 9 wherein:
the syringe has a cylindrical body and a plunger movable axially within the body between a first position corresponding to the reference volume and a second position corresponding to the calibration volume; and,
the system further comprises a mechanical stop engageable with the plunger in said first position to prevent the volume of the system from exceeding the reference volume during a measurement sequence.

11. A method for vascular examination of a limb comprising:
mounting at least one flexible-walled chamber of a pneumatic system to a limb for monitoring limb volume;
inflating the pneumatic system and thus the flexible-walled chamber to a preselected reference pressure;
maintaining the pneumatic system at the reference pressure for a preselected stabilization period by introducing and withdrawing air, as necessary, to permit temperature and volume conditions within the flexible-walled chamber and the limb to stabilize;
closing the pneumatic system to the atmosphere;
altering the volume of the pneumatic system by a preselected amount to achieve a calibration volume at a corresponding calibration pressure;
measuring and storing the calibration pressure; and
using the stored calibration pressure to display fluctuations in system pressure as changes in limb volume.

12. The method of claim 11 which further comprises:
storing the reference pressure for use with the calibration pressure in calibrating subsequent pressure fluctuations.

13. The method of claim 12 wherein the fluctuations in system pressure are displayed on a graphical output device which is calibrated to reflect changes in limb volume by:
sending signals representative of the reference pressure and the calibration pressure to the output device for display; and
adjusting the gain of said signals so that the reference pressure and the calibration pressure are displayed a preselected distance apart in a direction representing limb volume.

14. The method of claim 13 wherein calibration further comprises:
adjusting said signals so that the reference pressure is displayed at a preselected baseline level corresponding to the reference volume.

15. The method of claim 13 wherein:
the reference pressure and the calibration pressure are sent to the output device alternately for display during calibration without any other pressure signal.

16. The method of claim 11 which further comprises the step of:
returning the pneumatic system to the reference volume after the calibration pressure has been stored.

17. Apparatus for vascular examination of a limb, comprising:
a pneumatic system having:
at least one flexible-walled chamber mountable to a limb for monitoring limb volume;
a pressure sensor in communication with the flexible-walled chamber for measuring pressure in the system;
means for inflating the pneumatic system to a preselected reference pressure at a stable reference volume;
a valve for closing the pneumatic system to the atmosphere at said reference pressure; and,
means in communication with the flexible-walled chamber for altering the volume of the pneumatic system by a preselected amount to achieve a calibration volume at a corresponding calibration pressure;

means for storing the calibration pressure measured by the sensor; and graphical output means for using the stored calibration pressure to display fluctuations in system pressure as changes in limb volume;

means for alternately sending signals representative of the reference pressure and the calibration pressure to the output device for display; and means for adjusting the gain of said signals so that the reference pressure and the calibration pressure are displayed a preselected distance apart in a direction representing limb volume.

18. The apparatus of claim 17 which further comprises:

means for adjusting said signals so that the reference pressure is displayed at a preselected baseline level.

19. The apparatus of claim 18 wherein:

the means for adjusting the gain of said signals and the means for adjusting said signals so that the reference pressure is displayed at a preselected baseline level are automatic.

20. The apparatus of claim 17 wherein the means for inflating the pneumatic system to the reference pressure comprise:

means responsive to the pressure sensor for maintaining the pneumatic system at the reference pressure for a preselected period by introducing and withdrawing air, as necessary, to permit temperature and volume conditions within the flexible-walled chamber and the limb to stabilize.

21. A method for vascular examination of a limb comprising:

mounting at least one flexible-walled chamber of a pneumatic system to a limb for monitoring limb volume;

inflating the pneumatic system and thus the flexible-walled chamber to a preselected reference pressure at a stable reference volume;

closing the pneumatic system to the atmosphere;

altering the volume of the pneumatic system by a preselected amount to achieve a calibration volume at a corresponding calibration pressure;

measuring and storing the calibration pressure;

alternately sending signals representative of the reference pressure and the calibration pressure to the output device for display;

adjusting the gain of said signals so that the reference pressure and the calibration pressure are displayed a preselected distance apart in a direction representing limb volume; and using the stored calibration pressure to graphically display fluctuations in system pressure as changes in limb volume.

22. The method of claim 21 wherein calibration further comprises:

adjusting said signals so that the reference pressure is displayed at a preselected baseline level corresponding to the reference volume.

23. The method of claim 21 wherein:

the reference pressure and the calibration pressure are sent to the output device alternately for display during calibration without any other pressure signal.

24. The method of claim 21 wherein the step of inflating the pneumatic system to the reference pressure comprises:

sensing the pressure in the pneumatic system and maintaining it at the reference pressure for a preselected stabilization period to permit conditions within the flexible-walled chamber and the limb to stabilize.

* * * * *